(12) United States Patent
Tybinkowski et al.

(10) Patent No.: US 8,356,374 B2
(45) Date of Patent: Jan. 22, 2013

(54) POWERED TOOTHBRUSH WITH ASSOCIATED ORAL SOLUTION DISPENSER MECHANISM

(76) Inventors: Andrew P. Tybinkowski, Boxford, MA (US); Federico Castellucci, Weston, MA (US); L. Paul Lustig, Newton, MA (US)

( * ) Notice: Subject to any disclaimer, the term of this patent is extended or adjusted under 35 U.S.C. 154(b) by 0 days.

(21) Appl. No.: 12/220,312

(22) Filed: Jul. 22, 2008

(65) Prior Publication Data
US 2009/0113643 A1    May 7, 2009

Related U.S. Application Data

(63) Continuation of application No. 10/255,400, filed on Sep. 26, 2002, now Pat. No. 7,401,373.

(60) Provisional application No. 60/325,014, filed on Sep. 26, 2001.

(51) Int. Cl.
*A46B 13/04*    (2006.01)

(52) U.S. Cl. .......................................... 15/29

(58) Field of Classification Search ............. 15/24, 29; 433/215–216
See application file for complete search history.

(56) References Cited

U.S. PATENT DOCUMENTS

| | | | |
|---|---|---|---|
| 1,676,601 A | 7/1928 | Cavanaugh |
| 1,859,402 A | 5/1932 | Maher |
| 2,081,792 A | 5/1937 | Cassanos et al. |
| 2,162,447 A | 6/1939 | Seibel |
| 2,259,928 A | 10/1941 | Eaton |
| 2,283,781 A | 5/1942 | Aiken |
| 2,743,042 A | 4/1956 | Burgin |
| 2,807,818 A | 10/1957 | Taylor |
| 2,845,645 A | 8/1958 | Wishnefsky et al. |
| 2,900,650 A | 8/1959 | Rivero |
| 2,960,040 A | 11/1960 | Bischoff |
| 3,148,684 A | 9/1964 | Keeler |
| 3,217,720 A | 11/1965 | Cyzer |
| 3,372,426 A | 3/1968 | Schwartzman |
| 3,400,996 A | 9/1968 | Vandergrift |
| 3,417,762 A | 12/1968 | Hall |
| 3,864,047 A | 2/1975 | Sherrod |
| 3,910,706 A | 10/1975 | Del Bon |
| 3,936,200 A | 2/1976 | O'Rourke |
| 4,049,354 A | 9/1977 | O'Rourke |
| 4,124,316 A | 11/1978 | O'Rourke |
| 4,155,663 A | 5/1979 | Cerquozzi |
| 4,221,492 A | 9/1980 | Boscardin et al. |
| 4,236,651 A | 12/1980 | Meyer et al. |
| 4,580,588 A | 4/1986 | Swope, Jr. |
| 4,615,635 A | 10/1986 | Kim |
| 4,826,341 A | 5/1989 | Kwak |
| 4,850,730 A | 7/1989 | Jimenez et al. |
| 5,028,158 A | 7/1991 | Fey |
| 5,062,728 A | 11/1991 | Kuo |
| 5,208,933 A | 5/1993 | Lustig et al. |
| 5,338,124 A | 8/1994 | Spicer et al. |
| 5,346,324 A | 9/1994 | Kuo |
| 6,434,773 B1 | 8/2002 | Kuo |
| 6,648,641 B1 | 11/2003 | Viltro et al. |

OTHER PUBLICATIONS www.dictionary.com, definitions of "releasable".
USPTO Class Defintion of Class 402.

*Primary Examiner* — Laura C Guidotti
(74) *Attorney, Agent, or Firm* — Pandiscio & Pandiscio

(57) ABSTRACT

An oral solution dispenser apparatus for attachment to a powered toothbrush handle having a drive coupling mounted thereon, includes a housing adapted for attachment to the handle, the housing having a recess therein for receiving a cartridge containing the oral solution, a pump disposed in the housing for moving the oral solution from the cartridge, and an outlet nozzle extending from the housing and adapted to permit movement of the oral solution from the pump and from the housing. A head having bristles thereon is adapted to interconnect with the handle drive coupling and the housing outlet nozzle, to facilitate powered movement of the bristles and movement of the oral solution from the outlet nozzle to proximate the bristles.

7 Claims, 18 Drawing Sheets

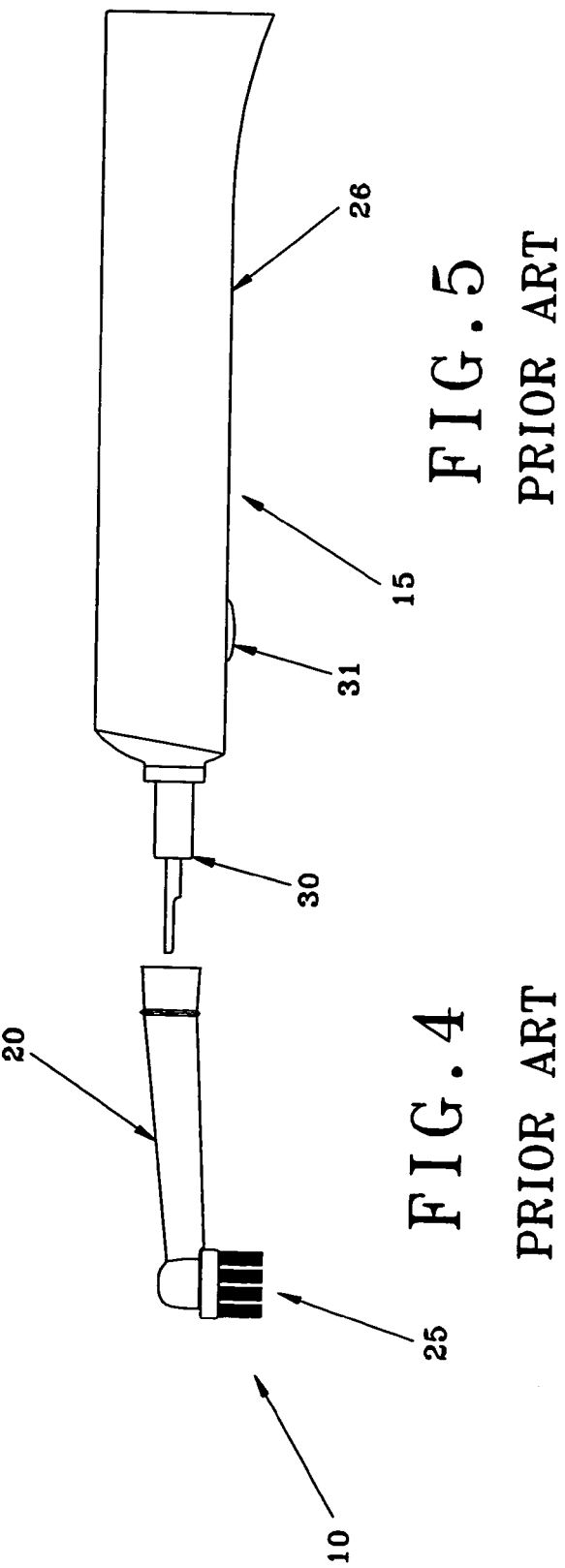

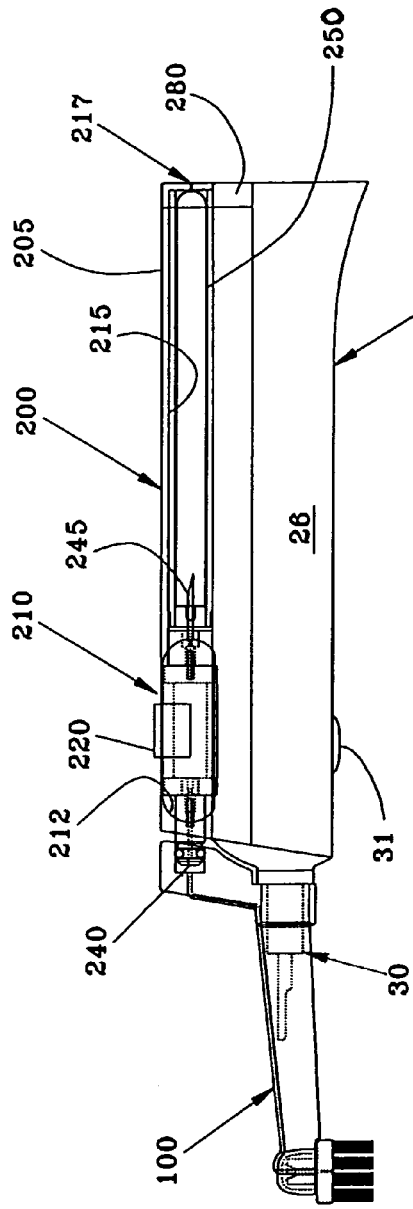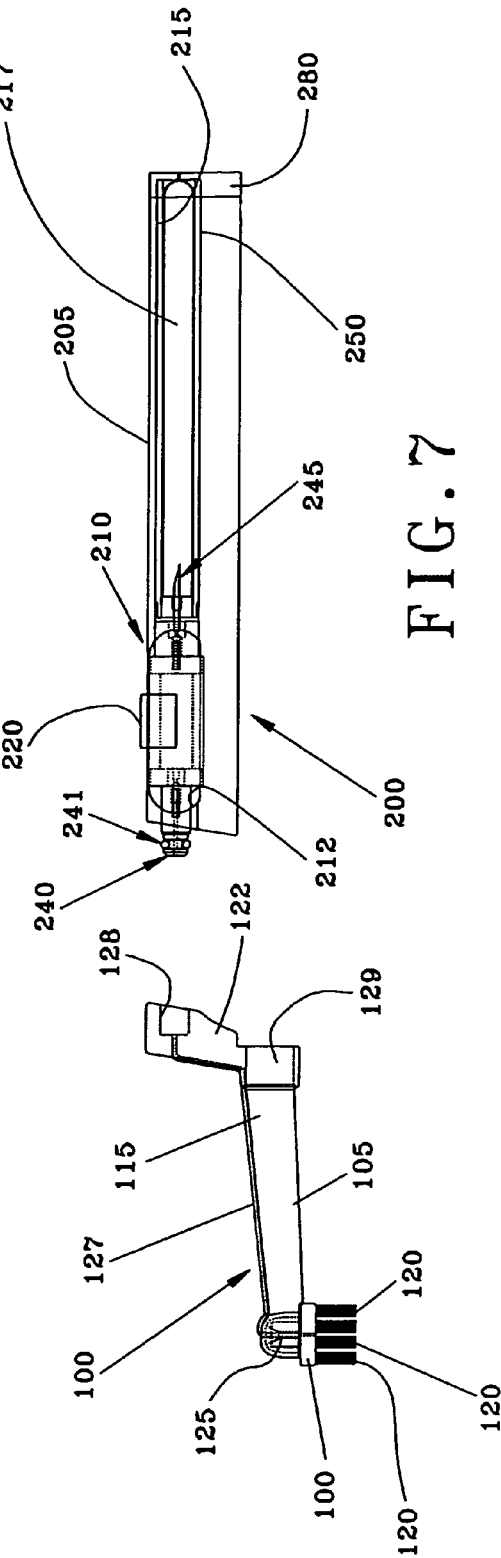

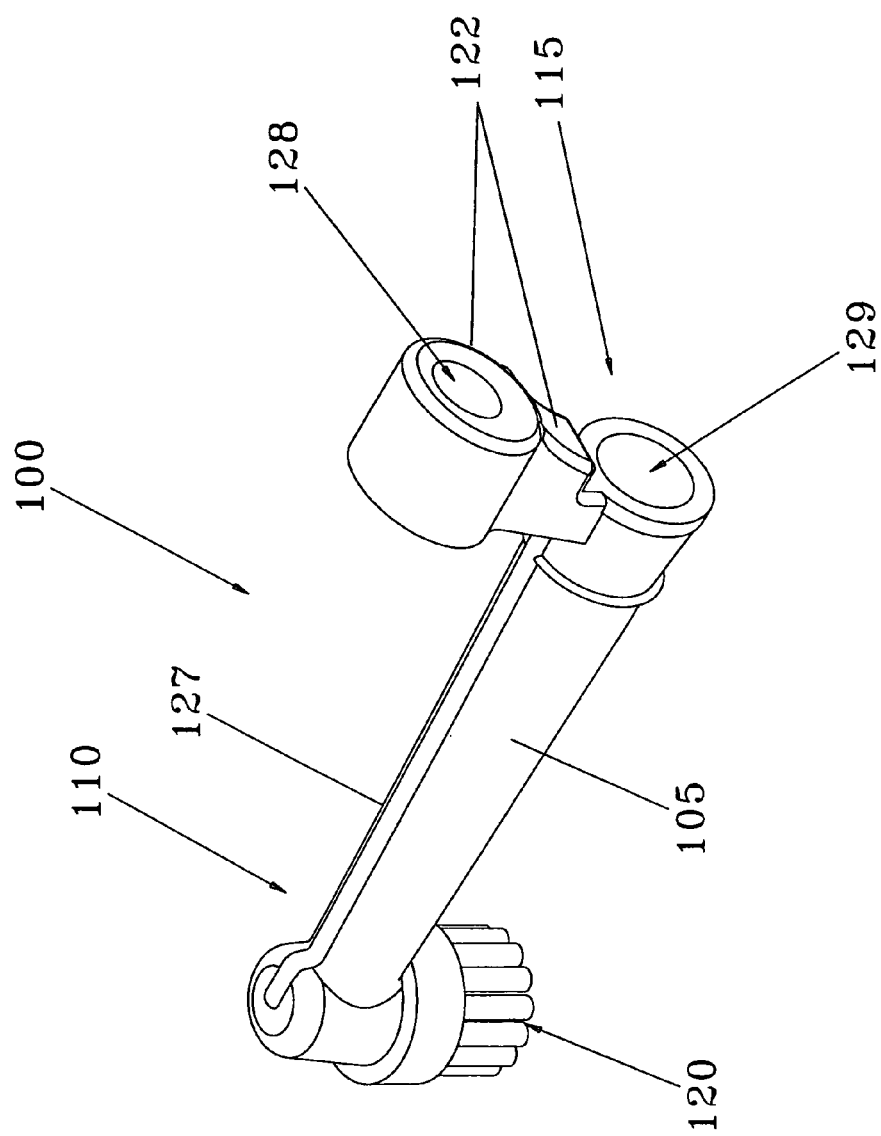

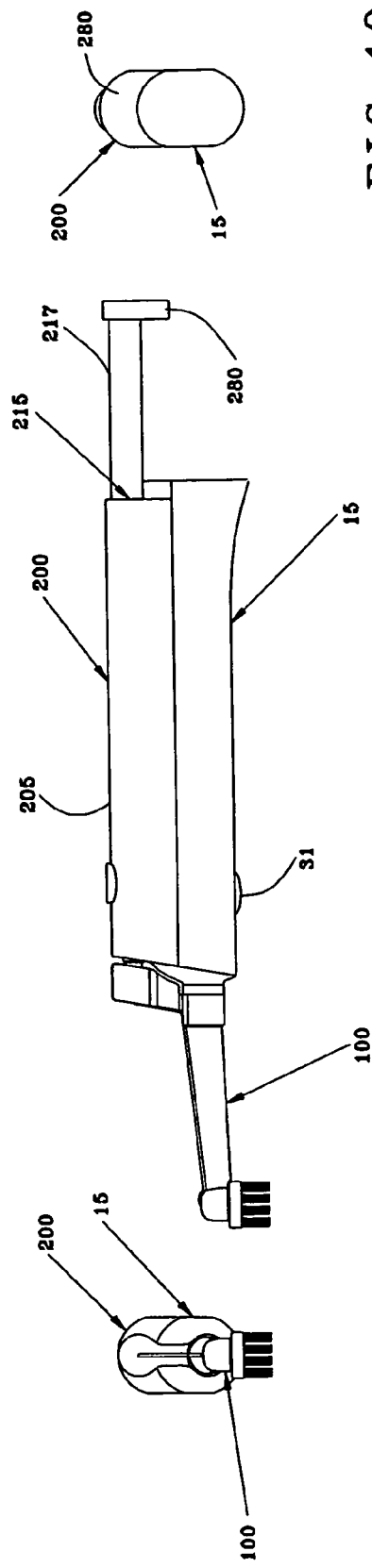

SCALE 2-1

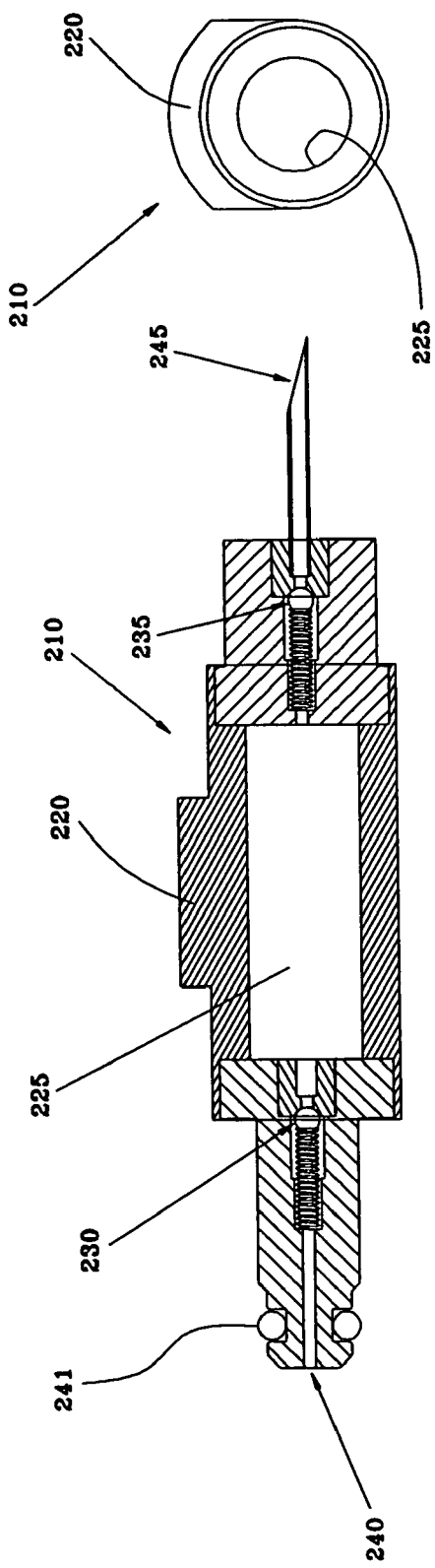

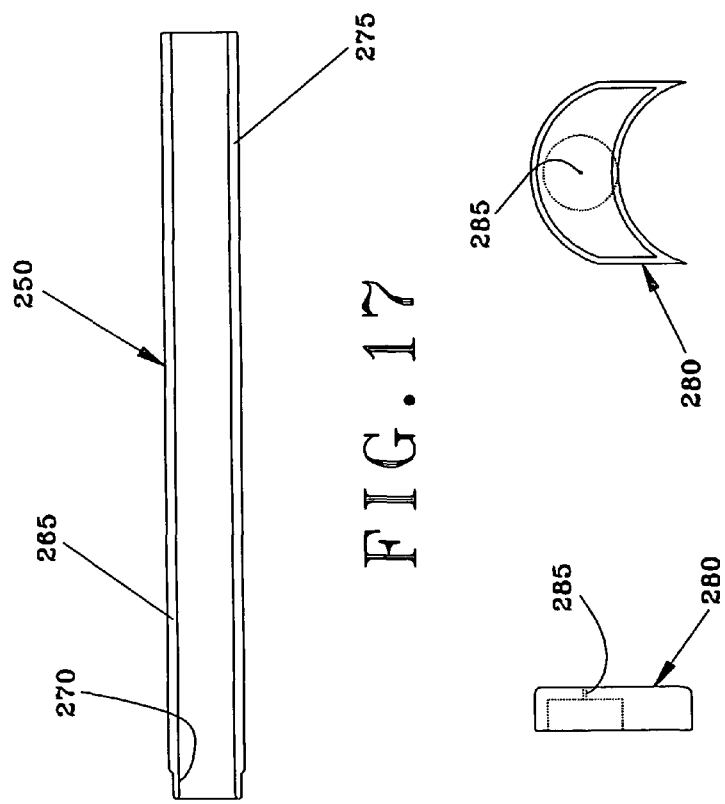

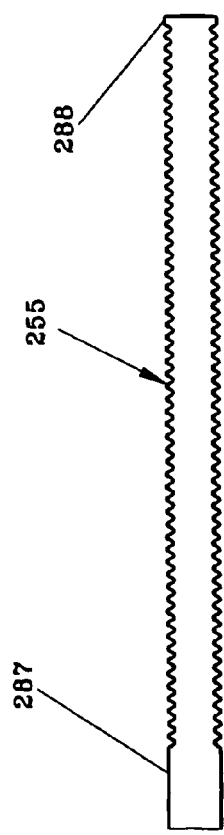
FIG. 20
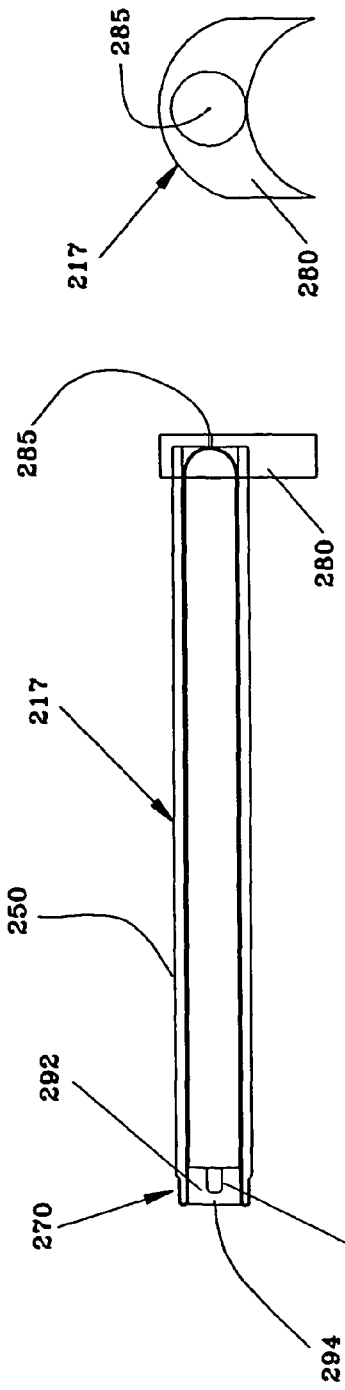
FIG. 21
FIG. 21 A

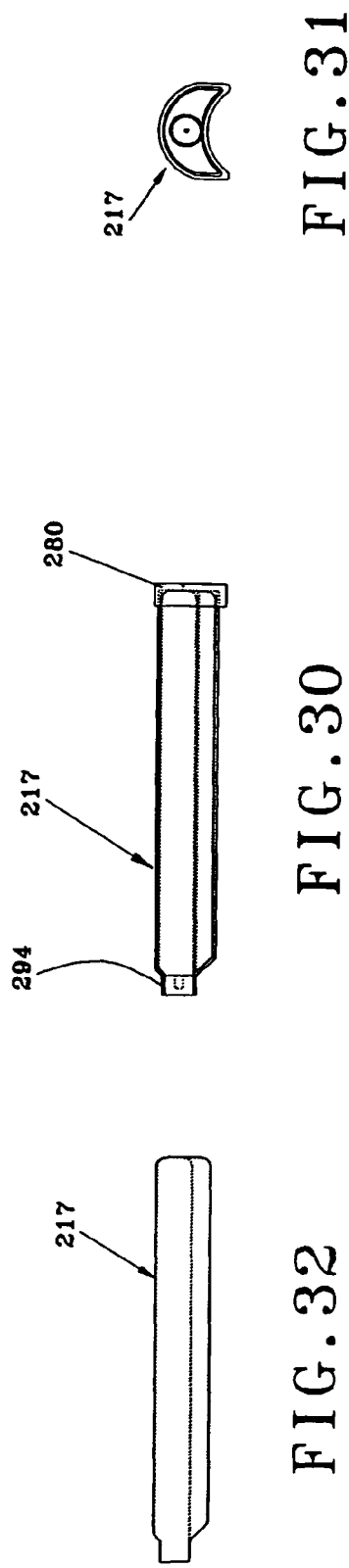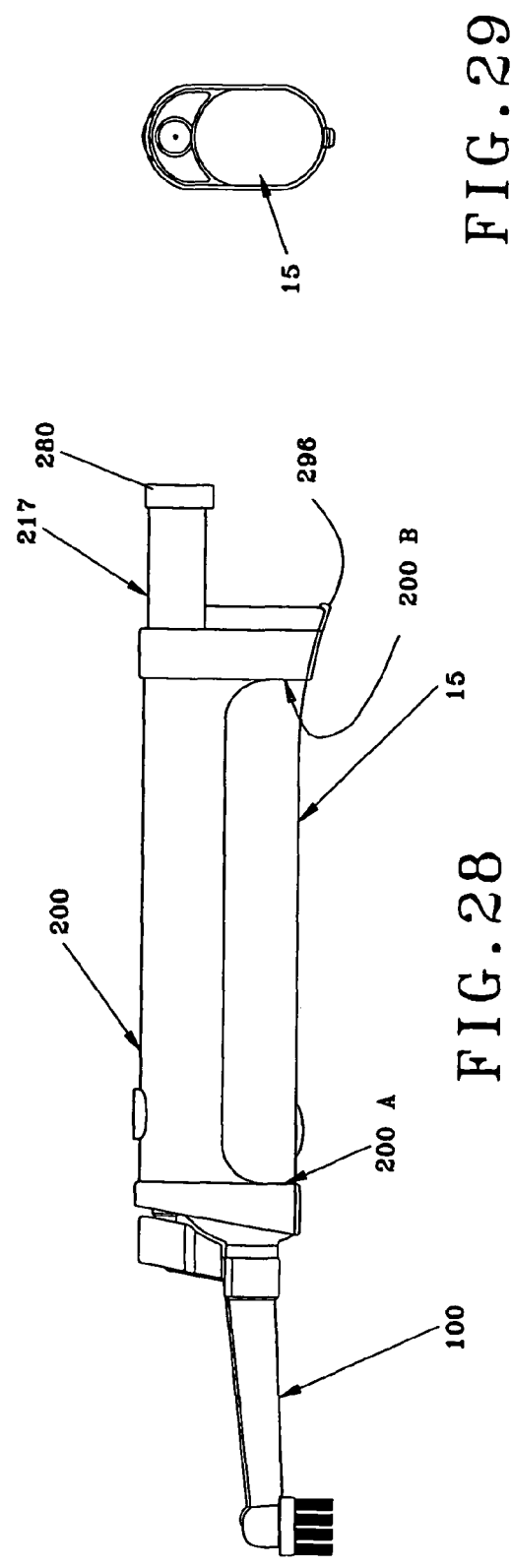

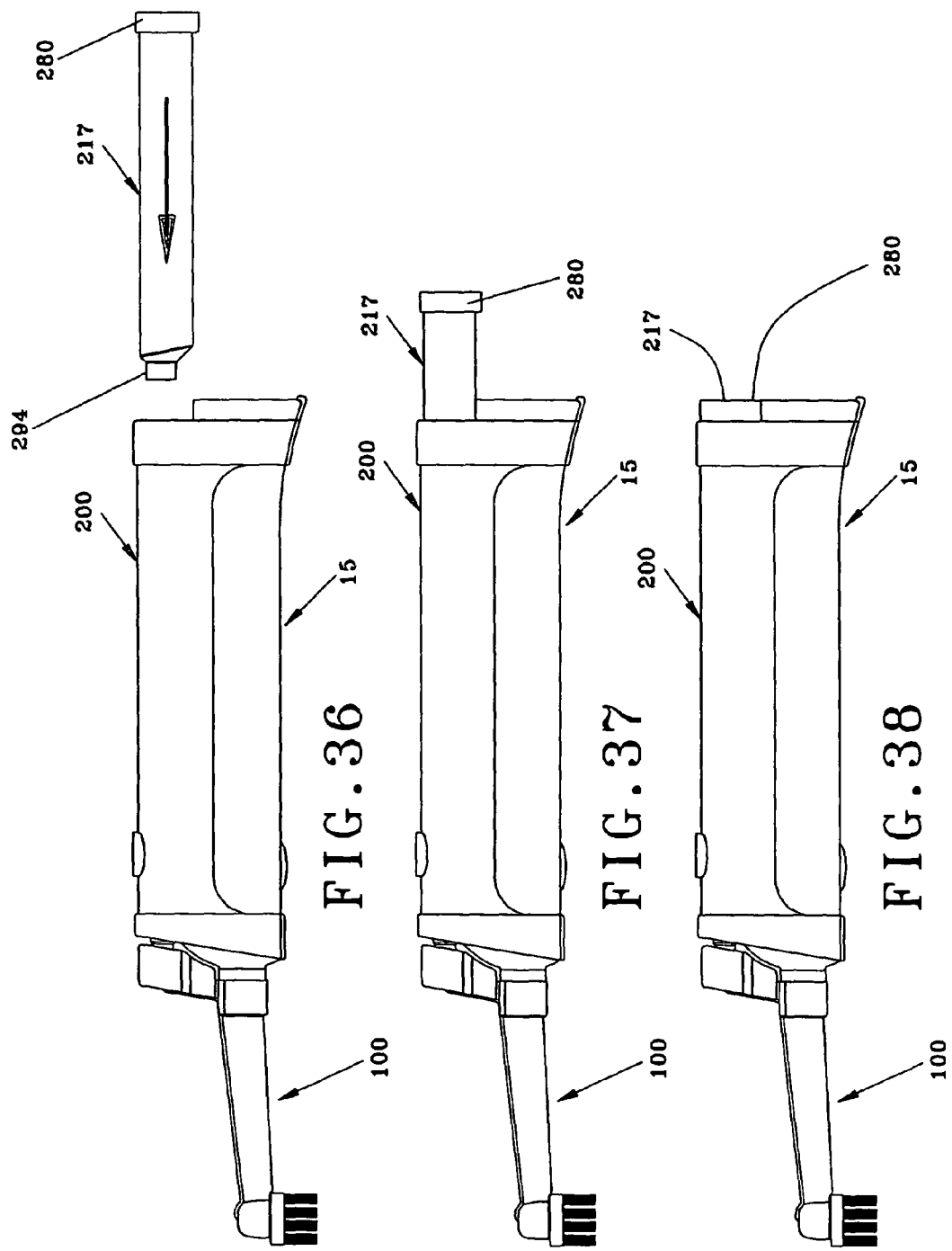

POWERED TOOTHBRUSH WITH ASSOCIATED ORAL SOLUTION DISPENSER MECHANISM

REFERENCE TO PENDING PRIOR PATENT APPLICATIONS

This patent application is a continuation of prior U.S. patent application Ser. No. 10/255,400, filed Sep. 26, 2002 now U.S. Pat. No. 7,401,373 by Andrew P. Tybinkowski et al, for POWERED TOOTHBRUSH WITH ASSOCIATED ORAL SOLUTION DISPENSER MECHANISM, which in turn claims benefit of prior U.S. Provisional Patent Application Ser. No. 60/325,014, filed Sep. 26, 2001 by Andrew P. Tybinkowski et al, for POWERED TOOTHBRUSH WITH ASSOCIATED FLUID DISPENSER MECHANISM The above-identified patent applications are hereby incorporated herein by reference.

FIELD OF THE INVENTION

This invention relates to dental apparatus in general, and more particularly to toothbrushes.

BACKGROUND OF THE INVENTION

Toothbrushes are well known in the art. In general, a toothbrush comprises a head having a plurality of bristles extending therefrom, and a handle adapted to be grasped by the hand of a user.

Powered toothbrushes are also well known in the art. In general, a powered toothbrush comprises a replaceable head having a plurality of bristles extending therefrom, and a handle adapted to be grasped by the hand of the user. The replaceable head is adapted to be removably mounted on the handle so that a driver mechanism located within the handle can drive the head longitudinally and/or laterally and/or rotationally, whereby to aid in brushing the teeth.

In the typical situation, dentifrice (e.g., toothpaste, tooth powder, etc.) is applied to the bristles of the toothbrush (either manual or powered) prior to the commencement of brushing. This is generally accomplished by grasping the handle of the toothbrush in one hand and the dentifrice container in the other hand, and then manually applying the dentifrice to the bristles of the toothbrush. Once the user has applied the dentifrice to the toothbrush, the user then commences brushing the teeth.

Thus, with conventional manual and powered toothbrushes, the dentifrice is generally held in a container separate from the toothbrush, and applying the dentifrice to the bristles of the toothbrush is a two-handed operation.

It has been recognized, for both manual and powered toothbrushes, that it would be advantageous to provide an improved toothbrush having a supply of liquid dentifrice located within the handle of the toothbrush, and a dispenser mechanism for dispensing the stored liquid dentifrice to the bristles of the toothbrush for application directly to the teeth.

In the past, there have been a number of proposals for achieving the foregoing, but all of these proposals are believed to suffer from one or more significant disadvantages, including ineffectiveness of operation, lack of durability, unattractiveness of appearance, prohibitive cost of manufacture, cross-contamination, etc.

Furthermore, with respect to powered toothbrushes, these proposals have generally required that the handle of the powered toothbrush be designed with dentifrice dispensing in mind. In other words, none of these proposals is believed to have addressed the issue of how a non-dentifrice-dispensing powered toothbrush can be quickly and easily converted into a dentifrice-dispensing powered toothbrush.

In addition to the foregoing, in some circumstances substances other than dentifrice may need to be applied to the teeth and/or to the tissue adjacent to the teeth (e.g., the gums) or to other tissue accessible by the oral cavity (e.g., the throat, etc.). By way of example, but not limitation, such substances may include whitening or bleaching agents, anticariogenic (i.e., anti-cavity) agents, such as fluoride, or medicinal agents, such as an antibacterial agent, a local or systemic antibiotic, etc. All such agents and dentifrices are collectively referred to hereinafter as "oral solutions". In this respect it should be appreciated that the term "solution" is not meant to be limiting, in the sense that it is intended to cover any flowable material consistent with the present invention, e.g., fluids, liquids, suspensions, gels, etc.

OBJECTS OF THE INVENTION

Accordingly, a primary object of the present invention is to provide an improved powered toothbrush having a supply of liquid oral solution associated with the handle of the toothbrush, and a dispenser mechanism for dispensing the stored solution to the bristles of the toothbrush for delivery directly to the teeth, both prior to and during brushing.

Another object of the present invention is to provide a oral solution dispensing toothbrush adapted to utilize replaceable, oral solution storing cartridges.

Another object of the present invention is to provide a solution dispensing toothbrush which is effective in operation, durable, attractive in appearance, and relatively inexpensive to manufacture.

Still another object of the present invention is to provide apparatus whereby a non-solution dispensing powered toothbrush can be quickly and easily upgraded into a dispensing powered toothbrush.

SUMMARY OF THE INVENTION

These and other objects of the present invention are addressed by the provision and use of a novel solution dispenser mechanism which can be used with the handle of a conventional powered toothbrush, whereby to quickly and easily provide a solution-dispensing powered toothbrush.

The solution dispensed by the dispenser mechanism may be in various states, e.g., liquids, gels, pastes, etc. Furthermore, the solution dispensed by the solution dispenser mechanism may serve a variety of functions, e.g., cleaning (such as dentifrice), whitening or bleaching (such as a bleaching agent), anticariogenic (i.e., anti-cavity, such as fluoride), medicinal (e.g., antibacterial), etc.

With the above objects in view, a feature of the invention is the provision of an oral solution dispenser apparatus for attachment to a powered toothbrush handle having a drive coupling mounted thereon. The apparatus comprises a housing adapted for attachment to the handle, the housing being adapted for receiving a cartridge containing the oral solution, a pump disposed on the housing for moving the oral solution from the cartridge, and an outlet nozzle mounted on the housing and adapted to permit movement of the oral solution from the pump and from the housing. A head having bristles thereon is adapted to interconnect with the handle drive coupling and the housing outlet nozzle, to facilitate powered movement of the bristles and movement of the oral solution from the outlet nozzle to proximate the bristles.

In accordance with a further feature of the invention, there is provided a powered toothbrush comprising: a handle having a drive coupling mounted thereon, a housing fixed to the handle, the housing being adapted for receiving a cartridge containing an oral solution, a pump disposed on the housing for moving the oral solution from the cartridge, an outlet nozzle mounted on the housing and adapted to permit movement of the oral solution from the pump and from the housing, and a head having bristles thereon and interconnected with the handle drive coupling and the housing outlet nozzle, whereby to facilitate powered movement of the bristles and movement of the oral solution from the cartridge to proximate the bristles.

In accordance with a still further feature of the invention, there in provided a method for simultaneously effecting oral scrubbing and the application of an oral solution. The method comprises the steps of providing a powered toothbrush handle having a drive coupling mounted thereon, and an oral solution dispenser apparatus comprising a housing adapted for attachment to the handle, the housing being adapted for receiving a cartridge containing the oral solution, a pump disposed on the housing for moving the oral solution from the cartridge, an outlet nozzle mounted on the housing and adapted to permit movement of the oral solution from the pump and from the housing, attaching the housing to the handle, providing a head having bristles thereon and interconnecting the head with the handle drive coupling and the housing outlet nozzle, providing a cartridge containing the oral solution and connecting the cartridge to the housing and into communication with the pump, activating the powered toothbrush drive coupling to effect powered movement of the bristles, and operating the pump to move the oral solution from the cartridge, through the pump and outlet nozzle, and out of the head proximate the bristles.

In accordance with a still further feature of the invention, there is provided a method for simultaneously effecting oral scrubbing and the application of an oral solution, the method comprising the steps of providing a powered toothbrush comprising a handle having a drive coupling mounted thereon, a housing fixed to the handle, the housing being adapted for receiving a cartridge containing an oral solution, a pump disposed on the housing for moving the oral solution from the cartridge, an outlet nozzle mounted on the housing and adapted to permit movement of the oral solution from the pump and on the housing, providing a head having bristles thereon and interconnecting the head with the handle drive coupling and the housing outlet nozzle, providing a cartridge containing the oral solution and connecting the cartridge to the housing and into communication with the pump, activating the powered toothbrush drive coupling to effect powered movement of the bristles, and operating the pump to move the oral solution from the cartridge, through the pump end outlet nozzle, and out of the head proximate the bristles.

BRIEF DESCRIPTION OF THE DRAWINGS

The above and other objects and features of the present invention will be more fully disclosed or rendered obvious by the following detailed description of the preferred embodiments of the invention, which is to be considered together with the accompanying drawings wherein:

FIGS. 1-5A illustrate a conventional powered toothbrush;

FIGS. 6-10 illustrate a novel replaceable head and a novel oral solution dispenser which are adapted to be mounted to the handle of the conventional powered toothbrush shown in FIGS. 1-5A;

FIGS. 15, 15A, 16 and 16A illustrate construction details of the novel dispenser shown in FIG. 7;

FIGS. 17-21 and 21A illustrate construction details of a cartridge for containing a supply of oral solution; and FIGS. 22-38 illustrate an alternative arrangement in which the novel dispenser is intended to be mounted to the handle of a conventional powered toothbrush while in the field.

DETAILED DESCRIPTION OF THE PREFERRED EMBODIMENT

Figures 1, 2, 3:
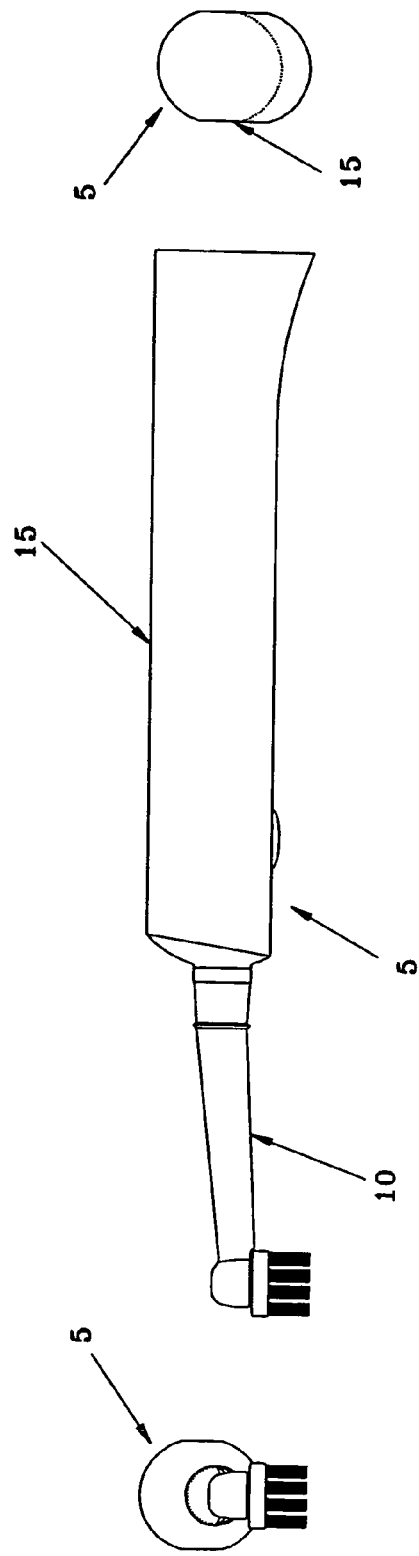
Figure 5A:
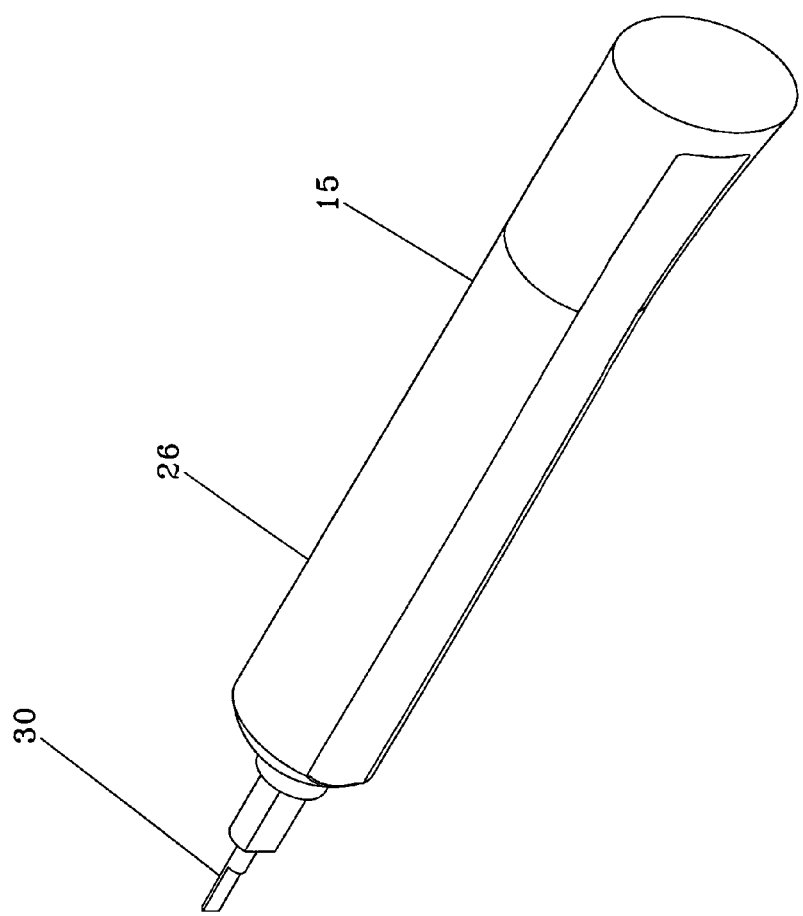
Figure 8A:
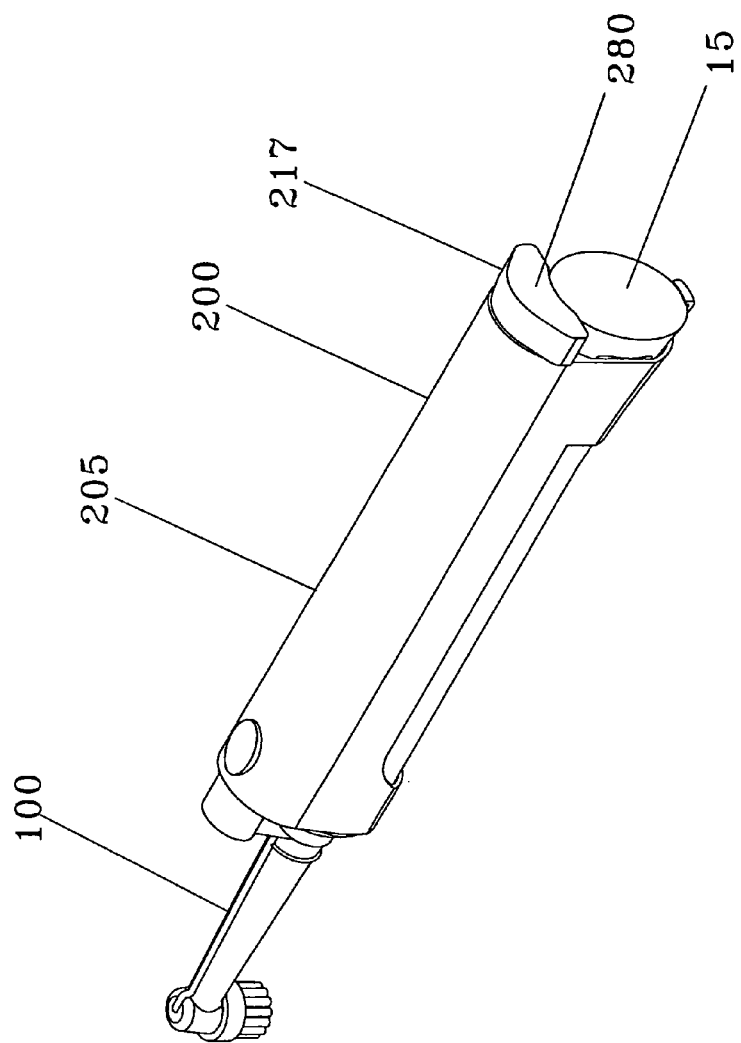
Figure 13:
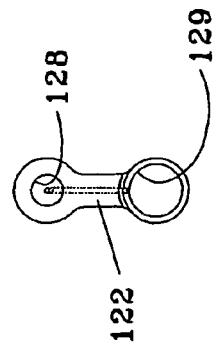
FIGS. 11-14 illustrate construction details of the novel replaceable head shown in FIGS. 6 and 6A.
Figure 12:
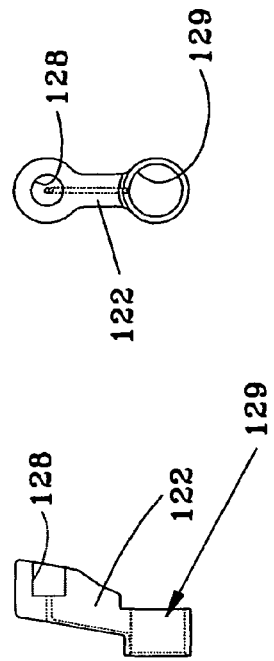
Figure 11:
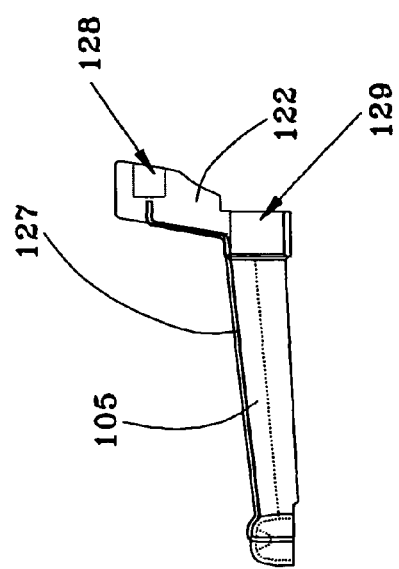
Figure 14:
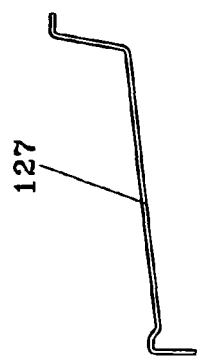
Figure 15:
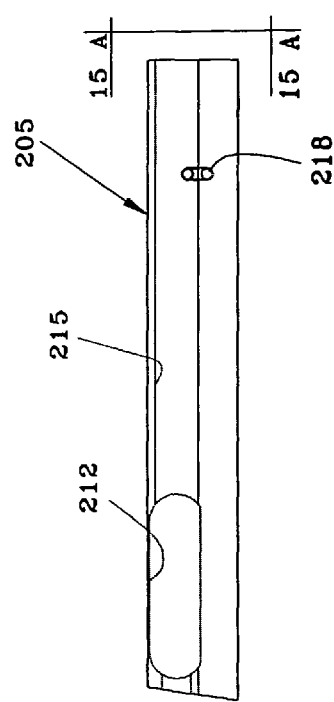
Figure 15:
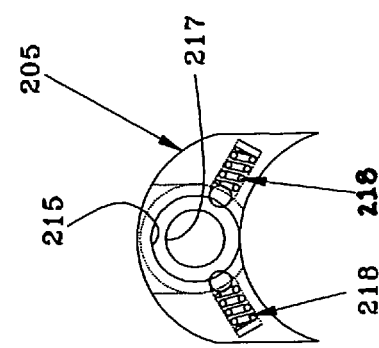
Figure 26:
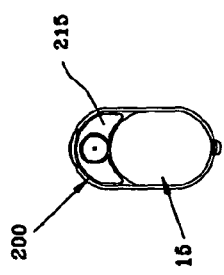
Figure 23:
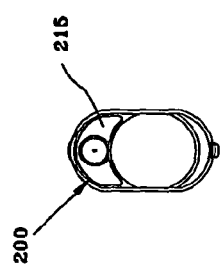
Figure 25:
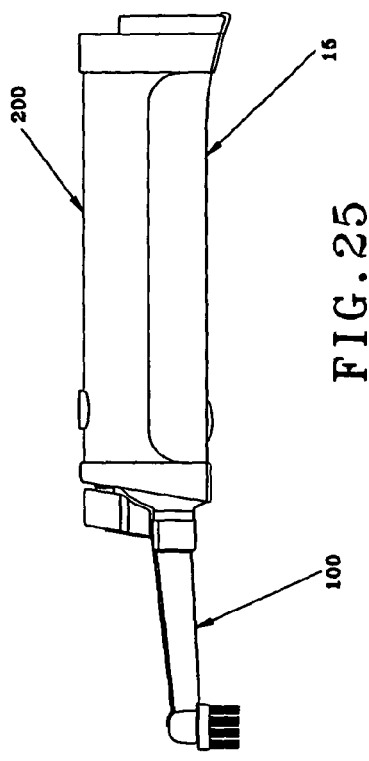

Looking first at FIGS. 1-5, there is shown a conventional powered toothbrush 5. Conventional powered toothbrush 5 generally comprises a replaceable head 10 and a handle 15. Replaceable head 10 (FIGS. 1, 2 and 4) generally comprises a stem 20 having a plurality of bristles 25 extending outwardly from a distal end thereof. Handle 15 (FIGS. 1, 3 and 5) has an elongated body 26 (FIG. 5) that includes a driver mechanism (not shown) located within the handle. This driver mechanism powers a drive coupling 30 (FIGS. 5 and 5A) extending out a distal end of handle body 26 whereby, when a replaceable head 10 is mounted on drive coupling 30 and the handle's driver mechanism is actuated, e.g., with button 31 (FIG. 5), the handle's driver mechanism can drive replaceable head 10 longitudinally and/or laterally and/or rotationally. Such driver mechanisms are of the sort well known in the art.

In accordance with the present invention, and looking now at FIGS. 6-10, there is provided a novel replaceable head 100 (FIGS. 6, 8, 9 and 9A) and a novel solution dispenser 200 (FIGS. 7, 8, 9, 9A and 10) which are adapted to be used with the handle 15 of a conventional powered toothbrush, whereby to provide a novel solution-dispensing powered toothbrush. As will be discussed in further detail below, novel replaceable head 100 is adapted to be mounted to the handle's drive coupling 30 whereby the replaceable head may be driven (e.g., longitudinally and/or laterally and/or rotationally) in the usual fashion. At the same time, however, novel replaceable head 100 is also adapted to receive a solution provided by solution dispenser 200, which is preferably formed integral with handle 15 or snap-mounted onto handle 15 or otherwise attached, so that solution may be dispensed to the bristles of the replaceable head 100 for application to the teeth. In accordance with the present invention, the solution dispensed by dispenser 200 may be in various states, e.g., liquids, gels, pastes, etc. Furthermore, the solution dispensed by dispenser 200 may serve a variety of functions, e.g., cleaning (such as dentifrice), whitening or bleaching (such as a bleaching agent), anticariogenic (i.e., anti-cavity, such as fluoride), medicinal (e.g., antibacterial), etc.

More particularly, and looking now at FIGS. 6, 6A and 11-14, replaceable head 100 comprises a stem 105 having a distal end 110 and a proximal end 115. A plurality of bristles 120 extend outwardly from stem 105 generally adjacent to the distal end of the stem. A mount 122 is connected to the proximal end 115 of the stem 105. A passageway 125 is formed in the distal end 110 of stem 105. One end of passageway 125 opens adjacent to, and preferably amidst, bristles 120, and the other end of passageway 125 connects to a fluid conduit 127 which runs along the length of the stem 105. The other end of fluid conduit 127 connects to a passageway 128 (FIGS. 6, 6A and 12) formed in mount 122. It will be appreciated that, on account of the foregoing construction, fluid introduced into passageway 128 in mount 122 may flow through that passageway, through fluid conduit 127, and then through passageway 125 so as to exit the stem adjacent to, and preferably amidst, bristles 120.

Stem 105 also includes an opening 129 (FIGS. 6 and 6A) in its proximal end 115, whereby replaceable head 100 may be mounted to the handle's drive coupling 30 (FIG. 8).

Looking next at FIGS. 8, 8A, 15, and 15A, fluid dispenser 200 comprises a housing 205 which generally includes a pump 210 received in a pump-receiving recess 212 (FIG. 15), and a cartridge-receiving recess 215 for receiving a cartridge 217 containing a supply of oral solution. A pair of spring-loaded ball detents 218 (FIG. 15A) releasably hold the cartridge 217 in cartridge-receiving recess 215.

Pump 210 (FIGS. 16, 16A) comprises at least one flexible wall 220 partially defining a central chamber 225, a pair of check valves 230, 235, an outlet port 240 (preferably including an O-ring seal 241 such as is shown in FIGS. 7 and 16 for sealing with the walls of passageway 128) and an inlet needle 245. Pump 210 essentially operates as follows:

(1) when needle 245 is in communication with an appropriate supply of oral solution, and the at least one flexible wall 220 is initially pressed inwardly, check valve 230 permits air inside chamber 225 to be expelled out outlet port 240 while check valve 235 prevents air inside chamber 225 from being expelled out through needle 245;

(2) when the at least one flexible wall 220 is thereafter released, check valve 235 permits solution to be drawn into chamber 225 through needle 245 while check valve 230 prevents air or fluid from being drawn into chamber 225 from outlet port 240;

(3) when the at least one flexible wall 220 is thereafter pressed inwardly again, check valve 230 permits fluid inside chamber 225 to be expelled out outlet port 240 while check valve 235 prevents air or fluid within chamber 225 from being expelled out through needle 245; and (4) when the at least one flexible wall 220 is thereafter released again, check valve 235 permits additional solution to be drawn into chamber 225 through needle 245 while check valve 230 prevents air or fluid from being drawn into chamber 225 from outlet port 240.

Thus, it will be seen that by connecting needle 245 to an appropriate supply of fluid, and by thereafter repeatedly depressing and releasing the pump's at least one flexible wall 220 in an in-and-out fashion, pump 210 causes fluid to be drawn from the oral solution supply and to be expelled from outlet port 240, while preventing fluid from being drawn into outlet port 240 and expelled out inlet needle 245.

Pump 210 (FIG. 16) is positioned in recess 212 (FIG. 15) in housing 205 so that the pump's outlet port 240 extends out the distal end of housing 205, and so that the pump's needle 245 extends into the housing's cartridge-receiving recess 215 (FIG. 7). In this way, when the proximal end of replaceable head 100 is connected to the distal end of housing 205, fluid leaving the pump's outlet port 240 can pass into passageway 128 of replaceable head 100 for subsequent delivery to the region of bristles 120. Additionally, when a cartridge 217 is disposed in the housing's cartridge-receiving recess 215, needle 245 can access the oral solution contained in cartridge 217.

Preferably, the relative dimensions of the Housing's cartridge-receiving recess 215 and needle 245 are coordinated with one another so that the sharp tip of needle 245 is safely shielded within recess 215 (FIGS. 7 and 8). In addition, the dimensions of recess 215 and needle 245 are preferably formed so that fingers, both large and small, will be prohibited from contacting the sharp tip of needle 245. This construction constitutes an important safety feature of the present invention.

In one form of the invention, solution dispenser 200 is intended to be permanently attached to, or formed integral with, powered toothbrush handle 15, e.g., such as at the time of the manufacture of powered toothbrush handle 15. Such a construction is shown in FIGS. 8-10. Alternatively, and as will hereinafter be discussed in detail below, solution dispenser 200 may be snap-mounted onto handle 15, or otherwise attached to handle 15, after manufacture of handle 15, e.g., by the user.

Cartridge 217 is shown in detail in FIGS. 8 and 17-21 and 21A. Cartridge 217 generally comprises a housing 250 (FIG. 17), a bladder 255 (FIG. 20) and a cap 260 (FIG. 21).

Referring to FIG. 17, it will be seen that the housing 250 comprises a hollow, elongated body 265 having a distal end 270 and a proximal end 275. Distal end 270 is open. Proximal end 275 is closed off by an element 280 (FIGS. 18 and 19) which includes a passageway 285 extending between the interior and exterior of body 265. Passageway 285 provides a path for air to pass into the interior of housing 250, as will hereinafter be described in further detail.

Referring to FIG. 20, it will be seen that the bladder 255 comprises an elongated body having a distal end 287 and a proximal end 288. Distal end 287 is open. Proximal end 288 is closed. The bladder's body is preferably formed with a bellows-like construction, which helps hold the body in the generally open (i.e., non-collapsed) shape shown in FIG. 20 prior to filling of the bladder with fluid. In addition, this construction helps keep the bladder's body open as fluid is withdrawn from the cartridge during use, so as to reduce the risk that some fluid may be trapped in the proximal portion of the bladder. In essence, this bellows-like construction helps provide directional control to the collapse of bladder 255 as fluid is withdrawn from the bladder, with bladder 255 collapsing primarily longitudinally rather than primarily radially.

Cap 260 is shown in FIG. 21. Cap 260 comprises a generally cylindrical resilient body 292 having a thin end wall section 294. On account of the foregoing construction, it will be appreciated that cap 260 comprises a relatively thin septum or seal for closing off the distal end of bladder 255, as will hereinafter be discussed. Furthermore, by forming cylindrical body 292 out of a resilient material, cap 260 can seal around needle 245 when the needle extends through the cap, as will hereinafter be discussed.

Cartridge 217 is intended to be assembled as follows. First, bladder 255 (FIG. 20) is inserted into the interior of housing 250 (FIG. 17). Then the distal end 287 of bladder 255 is pulled back over the outside of the distal end 270 of housing 250. In other words, the distal end of bladder 255 is everted so that it covers both the inside and outside surfaces of the distal end of housing 250. Then bladder 255 is filled with fluid. Finally, cap 260 (FIG. 21) is pressed into the mouth of housing 250 and bladder 255 so as to close off the interior of bladder 255.

The oral solution dispensing powered toothbrush is intended to be used as follows.

First, a replaceable head 100 is connected to handle 15 and dispenser 200, so that the handle's drive coupling 30 is in engagement with the replaceable head 100 (FIG. 8), and so that the dispenser's outlet port 240 is in communication with the replaceable head's passageway 128 (FIGS. 6, 6A). Then a fresh oral solution cartridge 217 is inserted into the dispenser 200. This is done by inserting cartridge 217, distal end first, into the housing's cartridge-receiving recess 215 (FIG. 9A). As cartridge 217 is advanced within the cartridge-receiving recess 215, the cartridge's cap 260 (FIG. 21) engages the sharp proximal tip of the pump's needle 245 and, upon further distal movement of cartridge 217, cap 260 is punctured by needle 245 (FIG. 8). Further distal movement of cartridge 217 continues until the cartridge is securely attached to fluid dispenser 200, with the solution in cartridge 217 being in communication with pump 210. Spring-loaded ball detents 218 (FIG. 15A) releasably hold cartridge 217 in cartridge-receiving recess 215.

Thereafter, in use, the user depresses and releases the pump's at least one flexible side wall 220 several times so as to manually advance solution from the interior of bladder 255, through pump 210, and out stem 105 amidst bristles 120, whereby the oral solution contained in bladder 255 will be applied to the teeth. In this respect, it will be appreciated that the two check valve construction of pump 210 permits solution to be supplied to bristles 120 regardless of the orientation of the toothbrush, i.e., the dispenser mechanism of the powered toothbrush operates successfully whether oriented horizontally, vertically, inverted, etc.

It will also be appreciated that, as solution is drawn out of bladder 255, housing passageway 285 (FIGS. 18, 19, 20 and 21) permits air to enter the interior of housing 265, whereby bladder 255 may easily release its fluid.

Furthermore, it will be appreciated that if, between brushing, the powered toothbrush should be laid down in a horizontal position while oral solution is in cartridge 217, no solution will leak from the toothbrush because of the two check valve construction of pump 210.

When the solution in cartridge 217 has been completely used up, or when it is thereafter desired to use a different cartridge 217 (e.g., one containing a different type of solution), cartridge 217 is detached from solution dispenser 200, whereupon a new cartridge 217 may be inserted.

As noted above, in one form of the invention solution dispenser 200 is intended to be permanently attached to, or formed integral with, powered toothbrush handle 15, e.g., such as at the time of the manufacture of powered toothbrush handle 15. Such a construction is shown in FIGS. 8-10.

Figure 22:
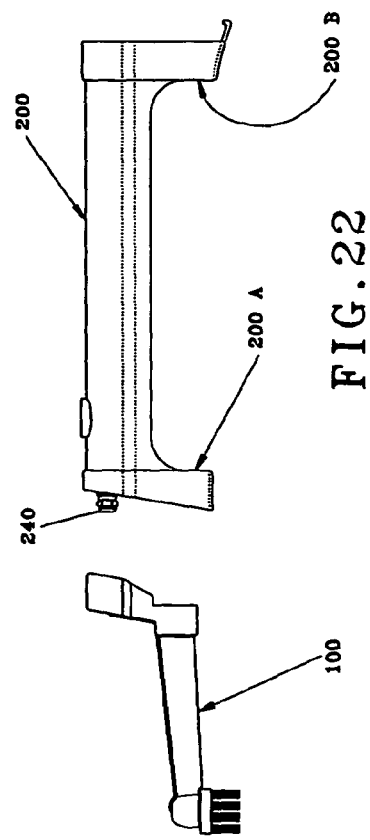
Figure 27:
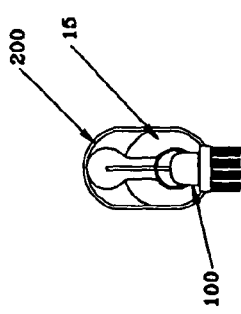
Figure 24:
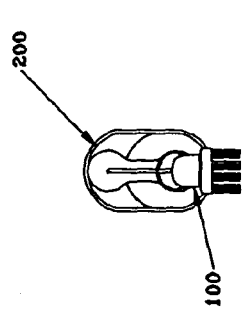
Figure 22A:
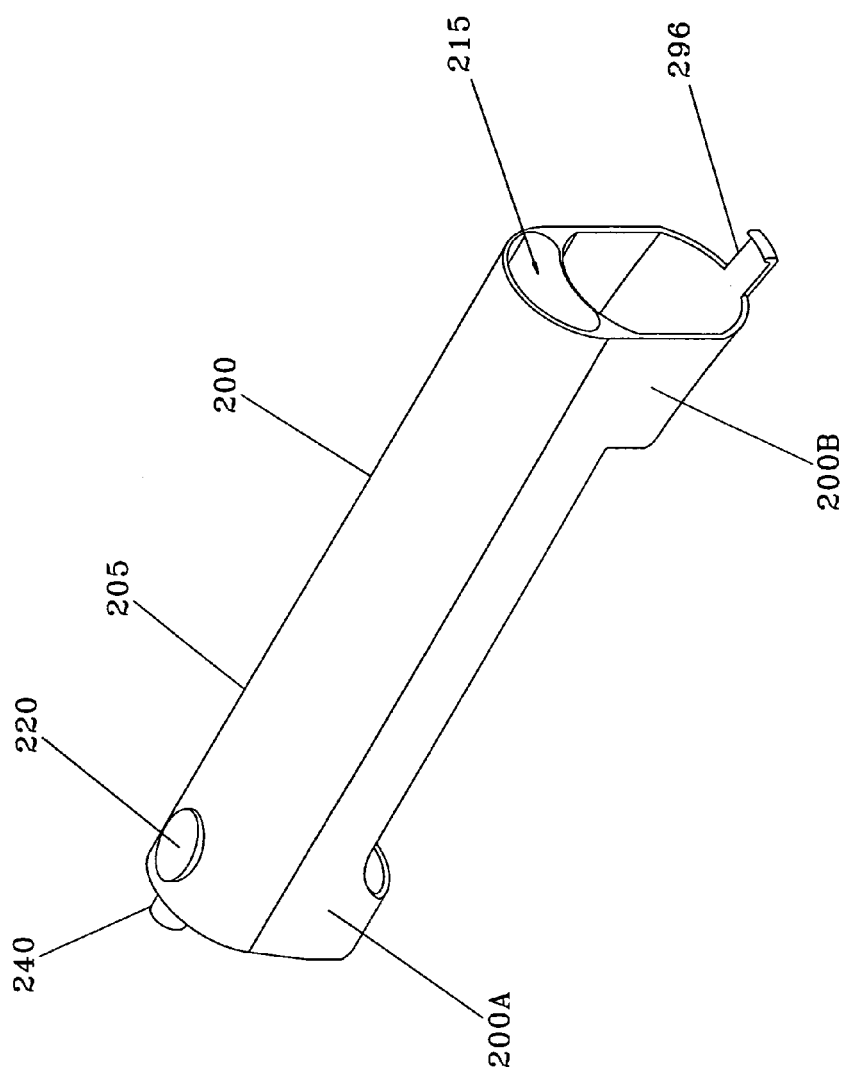
Figure 30A:
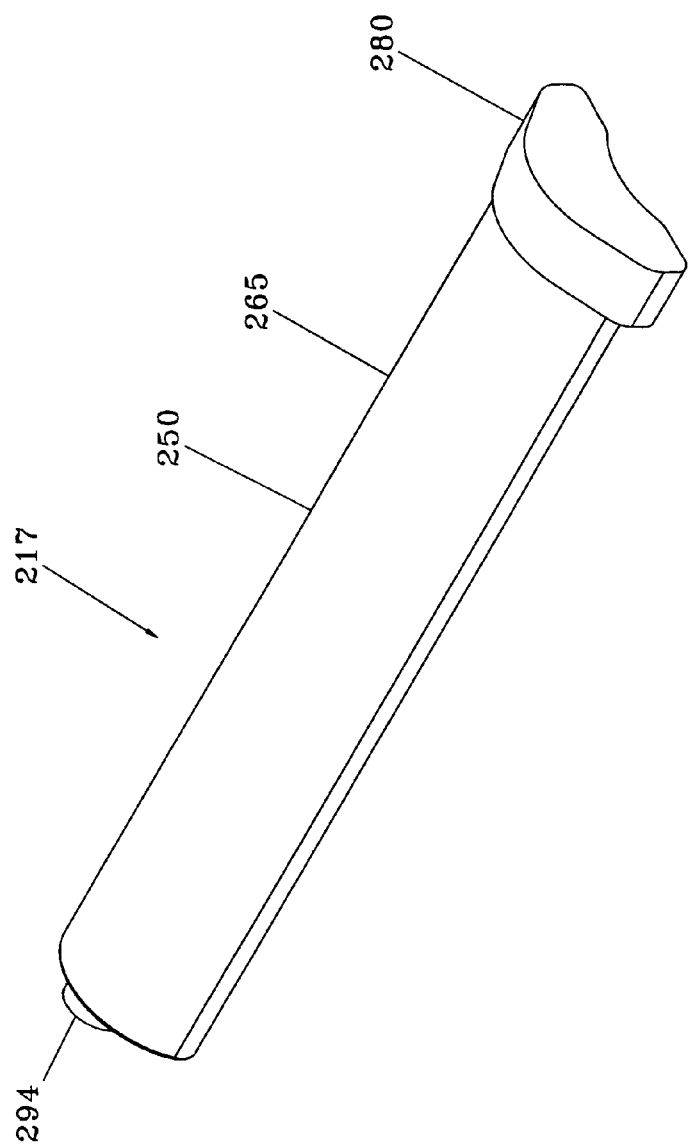
Figure 33:
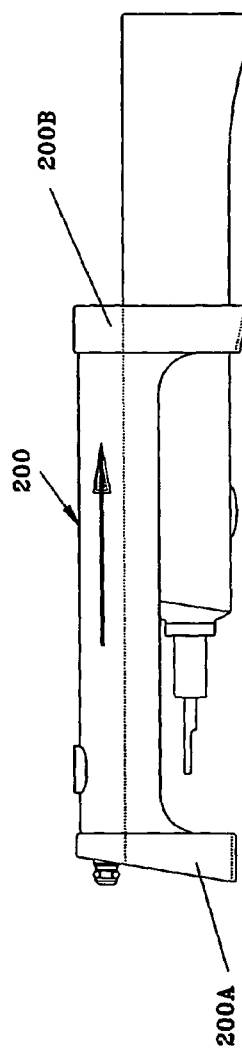
Figure 34:
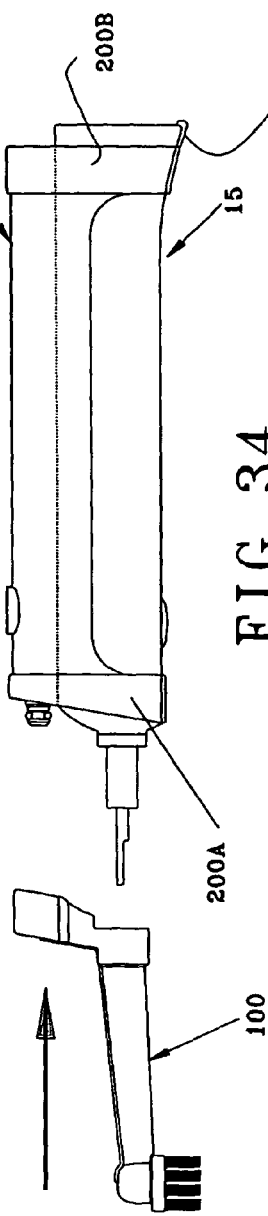
Figure 35:
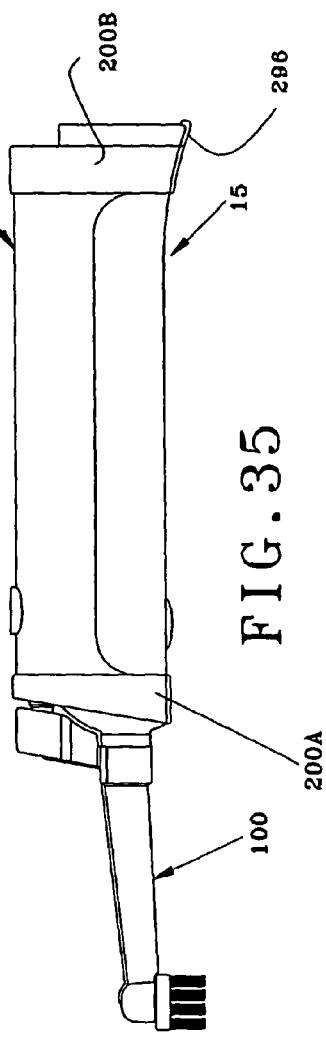

Alternatively, and as shown in FIGS. 22-38, dispenser 200 may be snap-mounted onto handle 15, or otherwise attached to handle 15, after manufacture of handle 15, e.g., by the user. Such a construction can be advantageous since it permits an existing powered toothbrush handle 15 to be retroactively converted into a solution dispensing powered toothbrush. Where dispenser 200 is to be snap-mounted onto handle 15, or otherwise attached to handle 15, after manufacture, dispenser 200 may include a pair of supports 200A and 200B (FIG. 22) for the connection to handle 15 (FIG. 28). In use, dispenser 200 is first secured to handle 15 (FIG. 33), as by sliding the handle 15 through the supports 200A, 200B, until the handle 15 is engaged by a leaf spring 296. Replaceable head 100 is then mounted to handle 15 and dispenser 200 (FIGS. 34 and 35), and then oral solution cartridge 217 is installed in dispenser 200 (FIGS. 36-38).

These and other variations of the present invention will be apparent to those skilled in the art in view of the present disclosure.

What is claimed is:

1. A method for simultaneously effecting oral scrubbing and the application of an oral solution, the method comprising the steps of:
   providing an oral solution dispenser for attachment to a closed toothbrush handle having a drive coupling disposed thereon, the oral solution dispenser comprising:
      a housing adapted for attachment to and removal from the closed toothbrush handle, parallel to the length of the handle, the housing being adapted to receive a consumable cartridge containing the oral solution;
      a manually-operated dose dispensing pump connected to the housing for moving a volume of the oral solution from the cartridge; and
      an outlet nozzle connected to the pump and adapted to permit movement of the oral solution from the pump;
   attaching the housing to the handle;
   providing a replaceable head having bristles thereon, and interconnecting the head with the handle drive coupling and the outlet nozzle, the head comprising a stem having a passageway for delivering the oral solution from the outlet nozzle to the bristles;
   providing a consumable cartridge containing the oral solution and connecting the cartridge to the housing and into communication with the pump;
   activating the drive coupling to effect powered movement of the bristles; and
   operating the pump to move the oral solution from the cartridge, through the pump and outlet nozzle, and out of the head proximate the bristles.

2. The method in accordance with claim 1 wherein the step of interconnecting the head with the handle drive coupling and the outlet nozzle comprises connecting a first connector of the head with the handle drive coupling and connecting a second connector of the head with the outlet nozzle.

3. The method in accordance with claim 1 wherein the step of connecting the cartridge to the housing and into communication with the pump comprises pushing a distal end of the cartridge into a recess in the housing and onto an inlet needle projecting proximally from the pump into the recess, to establish communication between the interior of the cartridge and the pump.

4. A method for simultaneously effecting oral scrubbing and the application of an oral solution, the method comprising the steps of:
   providing an oral solution dispenser apparatus for attachment to a toothbrush handle having a closed front end and having a drive coupling disposed thereon, the apparatus comprising:
      a housing adapted for releasable attachment to the handle, the housing extending alongside, and parallel to, at least a portion of the length of the handle, the housing being adapted to receive a consumable cartridge containing the oral solution;
      a manually-operated dispensing pump connected to the housing for moving the oral solution from the cartridge;
      an outlet nozzle connected to the dispensing pump and adapted to permit movement of the oral solution from the pump; and
      a head comprising a longitudinally extending stem having a distal end and a proximal end, the distal end of the stem having bristles thereon and the proximal end of the stem being adapted to releasably interconnect with the handle, the stem having a length sufficient to space the bristles from the handle, the stem having a passageway extending between a distal opening located on the distal end of the stem adjacent to the bristles and a proximal opening located on the proximal end of the stem, the proximal end of the stem releasably interconnecting with the drive coupling of the handle such that the drive coupling of the handle is adapted to move the stem and the bristles, and the proximal end of the stem releasably interconnecting the proximal opening of the passageway with the outlet nozzle of the handle for delivering the oral solution from the cartridge to the bristles;

wherein the housing is adapted to slidably receive the handle therein;

wherein the housing is provided with a spring lock for releasably locking the handle in the housing;

wherein the pump is provided with an inlet needle extending therefrom and adapted to penetrate a distal end of the cartridge to place the pump in communication with the oral solution in the cartridge;

wherein the pump is manually operable to move the oral solution from the cartridge to proximate the bristles;

providing a consumable cartridge containing the oral solution and connecting the cartridge to the housing and into communication with the pump; and operating the pump by manually compressing and releasing a flexible wall of the pump to move the oral solution from the cartridge, through the pump and outlet nozzle, and out of the head proximate the bristles.

5. The method in accordance with claim 4 wherein interconnecting the proximal end of the stem with the handle drive coupling and the outlet nozzle comprises connecting a first connector of the stem with the handle drive coupling and connecting a second connector of the stem with the outlet nozzle.

6. The method for simultaneously effecting oral scrubbing and the application of an oral solution in accordance with claim 4, wherein the method comprises the further step of:

activating the drive coupling to effect powered movement of the bristles.

7. The method in accordance with claim 4 wherein the step of connecting the cartridge to the housing and into communication with the pump comprises pushing a distal end of the cartridge into a recess in the housing and onto the inlet needle projecting proximally from the pump and into the recess, to establish communication between the interior of the cartridge and the pump.

* * * * *